United States Patent
Barnes, Jr. et al.

(10) Patent No.: US 6,334,886 B1
(45) Date of Patent: Jan. 1, 2002

(54) REMOVAL OF CORROSIVE CONTAMINANTS FROM ALKANOLAMINE ABSORBENT PROCESS

(75) Inventors: David Richard Barnes, Jr., Laurys Station; Arthur Daniel Bixler, Slatington, both of PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 09/569,732

(22) Filed: May 12, 2000

(51) Int. Cl.[7] .............................................. B01D 53/14
(52) U.S. Cl. ............................ 95/181; 95/183; 95/186; 95/187; 95/190; 95/235; 95/236; 96/234; 210/662; 210/670; 210/673; 210/677; 210/681; 210/683; 423/228
(58) Field of Search .................................. 210/662, 670, 210/673, 677, 681, 683; 423/228, 229; 95/181, 183, 186, 187, 190, 235, 236; 96/234

(56) References Cited

U.S. PATENT DOCUMENTS

| | | | |
|---|---|---|---|
| 2,797,188 A | 6/1957 | Taylor, Jr. et al. ............. 196/32 |
| 3,984,314 A | 10/1976 | Fries ........................ 210/30 R |
| 4,122,149 A | 10/1978 | Dunnery et al. ............. 423/242 |
| 4,170,628 A | 10/1979 | Kosseim et al. ............. 423/243 |
| 4,477,419 A | 10/1984 | Pearce et al. ................ 423/228 |
| 4,758,311 A | 7/1988 | Pagani et al. .................... 203/7 |
| 4,795,565 A | 1/1989 | Yan ............................ 210/669 |
| 4,970,344 A | 11/1990 | Keller ........................ 564/497 |
| 4,999,113 A | 3/1991 | Weber ........................ 210/664 |
| 5,006,258 A | 4/1991 | Veatch et al. ............... 210/677 |
| 5,045,291 A | * 9/1991 | Keller |
| 5,108,551 A | * 4/1992 | Yan |
| 5,137,702 A | * 8/1992 | Yan |
| 5,162,084 A | 11/1992 | Cummings et al. .......... 210/662 |
| 5,190,662 A | * 3/1993 | Keller et al. ................. 210/673 |
| 5,268,155 A | * 12/1993 | Yan |
| 5,277,822 A | 1/1994 | Higgins ...................... 210/673 |
| 5,292,493 A | * 3/1994 | Audeh et al. |
| 5,368,818 A | * 11/1994 | Cummings et al. |
| 5,393,505 A | * 2/1995 | Audeh |
| 5,607,594 A | * 3/1997 | Pohl et al. |
| 5,788,864 A | 8/1998 | Coberly et al. .............. 210/670 |
| 5,846,503 A | * 12/1998 | Yan |
| 6,071,484 A | * 6/2000 | Dingman, Jr. et al. |
| 6,245,128 B1 | * 6/2001 | George, Jr. |

OTHER PUBLICATIONS

"Controlling Corrosion In Amine Treating Plants", Nielsen, et al., Proc. Laurance Reid Gas Cond. Conf. 45th, pp. 182–212 (1995).

* cited by examiner

Primary Examiner—Duane S. Smith
(74) Attorney, Agent, or Firm—Geoffrey L. Chase

(57) ABSTRACT

A process is provided for removing $CO_2$ and/or $H_2S$ from a gas mixture containing as impurities $CO_2$ and/or $H_2S$ and at least one other impurity selected from the group consisting of a cyanide and ammonia. The process includes contacting at least a portion of the reflux stream from the overhead vapor from a stripping column of an acid gas removal solvent (i.e., alkanolamine) treatment plant with an anion exchange resin to remove corrosive impurities. The ion-exchanged reflux stream is then recycled to the top of the stripping column or into the bulk circulating acid gas removal solvent (i.e., alkanolamine) passing from the bottom of the stripping column.

13 Claims, 3 Drawing Sheets

REMOVAL OF CORROSIVE CONTAMINANTS FROM ALKANOLAMINE ABSORBENT PROCESS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

This invention relates to alkanolamine sweetening facilities for processing gases containing ammonia and/or a cyanide, and more particularly to methods for neutralizing corrosive constituents that accumulate in the reflux stream of such facilities.

Alkanolamine sweetening facilities are commonly used to remove $H_2S$ and $CO_2$ from a variety of gases, including natural gases, enhanced oil recovery gases, refinery hydrodesulfurizer recycle gases, FCCU and Coker gas plant tail gases, LPG streams and Claus sulfur recovery tail gases. Such facilities include an absorber, in which $H_2S$ and $CO_2$ are dissolved in an aqueous solution of an alkanolamine to form solvated alkanolamine salts (erg., protonated alkanolamine cation with $HS^-$ and $HCO_3^-$ anions). The alkanolamine salts of $H_2S$ and $CO_2$ are not heat stable and are decomposed by steam stripping in a stripping column, with the concomitant removal of the released $H_2S$ and $CO_2$ and deprotonation of the alkanolamine, freeing it for repeated reaction with acid gas in the absorber.

Unfortunately, alkanolamine salts are also formed with anions of other strong and weak acids that accumulate in the circulating solution. These may derive from gases, such as $SO_2$, COS, or HCN, which are present in the hydrocarbon gases through reactions in the alkanolamine solution. These additional alkanolamine salts cannot be removed by steam stripping, unlike $H_2S$ and $CO_2$ salts, and thus they are called heat stable salts. Heat stable salts remain in the system where they accumulate in the alkanolamine solution, gradually depleting the effectiveness of alkanolamine treatment. In addition, high concentrations of heat stable anions in the alkanolamine solution corrode the carbon steel components of the system. The corrosion products are also known to contribute to foaming problems in the system which further decreases treating effectiveness and causes amine losses. Various attempts have been made at solving these problems. See, e.g., Nielsen et al., AControlling Corrosion in Amine Treating Plants,@ Proc. Laurance Reid Gas Cond. Conf. 45th, pp. 182–212 (1995).

It has been proposed to remove heat stable salts from the lean alkanolamine solution exiting the bottom of the stripping column by ion exchange filtration. See, e.g., U.S. Pat. Nos. 2,797,188, 4,122,149, 4,170,628, 4,477,419, 4,758,311, 4,795,565, 4,970,344, 4,999,113, 5,006,258, 5,162,084, 5,277,822 and 5,788,864. Generally, heat stable salt anions are removed by exchange with hydroxide from an anion exchange resin and cations, such as sodium and potassium, are removed by exchange with hydrogen ion from a cation exchange resin. In the anion case, the protonated amine from the heat stable salt is deprotonated by reaction with hydroxide from the resin, resulting in water and free amine capable of reacting with acid gases.

Despite the foregoing developments, there is still room for improvement in the art. In particular, it is desired to reduce the amount of alkanolamine lost in the alkanolamine regeneration process. It is further desired to extend the time that the ion exchange resin can be onstream prior to regeneration. It is still further desired to provide a method for neutralizing corrosive constituents that can accumulate in the stripping column reflux stream of an alkanolamine facility processing synthesis gas feedstocks containing ammonia and or cyanides.

All references cited herein are incorporated herein by reference in their entireties.

BRIEF SUMMARY OF THE INVENTION

Accordingly, a process is provided for removing $CO_2$ and/or $H_2S$ from a gas mixture containing as impurities $CO_2$ and/or $H_2S$ and at least one other impurity selected from the group consisting of a cyanide and/or ammonia, the process comprising:

conveying the gas mixture to an absorber vessel in which the gas mixture is contacted with an aqueous absorbent solution containing an acid gas removal solvent, such as an alkanolamine, to remove $CO_2$ and/or $H_2S$ from the gas mixture and form a rich aqueous absorbent solution enriched in $CO_2$ and/or $H_2S$ removed from the gas mixture;

conveying the rich aqueous absorbent solution from the absorber vessel to a stripping vessel in which $CO_2$ and/or $H_2S$ are thermally stripped from the rich aqueous absorbent solution to form a lean aqueous absorbent solution depleted of $CO_2$ and/or $H_2S$, and an overhead vapor stream rich in $CO_2$ and/or $H_2S$ and the at least one other impurity;

recycling the lean aqueous absorbent solution from the stripping vessel to the absorber vessel to absorb additional amounts of the gas mixture;

cooling the overhead vapor stream in a heat exchanger and separating the resulting two phase stream in a separator vessel to provide an acid gas rich vapor stream and an alkanolamine rich aqueous solution; and contacting at least a portion of the alkanolamine rich aqueous solution with an anion exchange resin to remove from the alkanolamine rich aqueous solution at least a part of at least one other impurity prior to recycling the alkanolamine rich aqueous solution for further use in the process.

Also provided is an apparatus adapted to perform the process of the invention. A preferred embodiment of the apparatus of the invention comprises:

an absorber vessel comprising a sour gas mixture inlet and a rich aqueous absorbent solution outlet below a purified gas outlet and an acid gas removal solvent rich aqueous solution inlet;

a stripping vessel comprising in order from top to bottom, an overhead vapor stream outlet, a recycled reflux inlet, a rich aqueous absorbent solution inlet and a lean aqueous absorbent solution outlet, wherein said rich aqueous absorbent solution inlet is in fluid communication with said rich aqueous absorbent solution outlet and said lean aqueous absorbent solution outlet is in fluid communication with said acid gas removal solvent rich aqueous solution inlet;

a heat exchanger comprising an overhead vapor stream inlet and a two phase outlet on one side and a coolant stream inlet and a coolant stream outlet on the other side, wherein said overhead vapor stream inlet is in fluid communication with said overhead vapor stream outlet;

a separator vessel comprising in order from top to bottom, an acid gas rich stream outlet, a two phase stream inlet, and an acid gas removal solvent rich aqueous solution outlet, wherein said two phase stream inlet is in fluid communication with said two phase stream outlet and said acid gas removal solvent rich aqueous solution outlet is in fluid communication with said recycled reflux inlet; and a resin bed comprising said anion exchange resin, a resin bed inlet, and a resin bed outlet, wherein said resin bed inlet is in fluid communication with said acid gas removal solvent rich aqueous solution outlet, and said resin bed outlet is in fluid communication with said acid gas removal solvent rich aqueous solution inlet.

An alternative embodiment of the apparatus comprises:

an absorber vessel comprising a sour gas mixture inlet and a rich aqueous absorbent solution outlet below a purified gas outlet and an acid gas removal solvent rich aqueous solution inlet;

a stripping vessel comprising in order from top to bottom, a rich reflux gas outlet, a recycled reflux inlet, a rich aqueous absorbent solution inlet and a lean aqueous absorbent solution outlet, wherein said rich aqueous absorbent solution inlet is in fluid communication with said rich aqueous absorbent solution outlet and said lean aqueous absorbent solution outlet is in fluid communication with said acid gas removal solvent rich aqueous solution inlet;

a heat exchanger comprising an overhead vapor stream inlet and a two phase outlet on one side and a coolant stream inlet and a coolant stream outlet on the other side, wherein said overhead vapor stream inlet is in fluid communication with said overhead vapor stream outlet;

a separator vessel comprising in order from top to bottom, an acid gas rich stream outlet, a two phase stream inlet, and an acid gas removal solvent rich aqueous solution outlet, wherein said two phase stream inlet is in fluid communication with said two phase stream outlet; and a resin bed comprising said anion exchange resin, a resin bed inlet, and a resin bed outlet, wherein said resin bed inlet is in fluid communication with said acid gas removal solvent rich aqueous solution outlet, and said resin bed outlet is in fluid communication with said recycled reflux inlet.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

The invention neutralizes corrosive constituents that can accumulate in the reflux stream of an acid gas removal solvent (i.e.,alkanolamine) facility processing feedstocks containing ammonia and/or cyanides. Such feedstocks include gas streams from, e.g., syngas plants, Delayed Cokers, Visbreakers, Fluid Catalytic Cracking Units, hydrotreating plants, hydrocracking plants, and natural gas pipelines. Accordingly, the invention is suitable for treating gas mixtures comprising $CO_2$, $H_2S$, and at least one of cyanide and ammonia. The invention is particularly well-suited to removing ammonium carbamate generated by feedstocks containing ammonia and CO. The gas mixture can additionally contain, e.g., at least one member selected from the group consisting of carboxylic acids.

The invention improves upon the conventional practice of disposing of a portion of the reflux stream containing not only the corrosive constituents but also significant amounts of acid gas removal solvent (i.e., alkanolamine) and water. Rather than having to dispose of a continuous waste stream, the invention only requires disposing of a stream containing the neutralized impurities during the infrequent regeneration of the resin bed. Moreover, the invention obviates the need to replenish acid gas removal solvent (i.e., alkanolamine) and water lost to purging.

An anionic exchange resin is used in the stripping column reflux stream to remove corrosive contaminants and prevent build-up of such contaminants, as opposed to other mechanical means, such as purging or stripping. The resin is selective in the removal of corrosive contaminants as it is used in the reflux stream. The prior art has used anionic resin beds for removing contaminants (typically less corrosive amine compounds, known as heat stable salts) from the bulk circulating acid gas removal solvent (i.e., alkanolamine) solution, without successfully preventing the corrosion of the stripping column overhead. As large quantities of heat stable salts are usually present, removal of contaminants from the bulk solution to a level needed to prevent buildup of other more aggressive corrosive substances, such as ammonium carbamate, are impracticable and ineffective.

The invention is preferably targeted to improved monoethanolamine systems, but the invention is also effective with other acid gas removal solvents, alkanolamine and amine systems, including, e.g., diethanolamine, methyl diethanolamine, diisopropanol amine, triethanol amine triethanol amine, methanol, potassium carbonate, diglycolamine, propylene carbonate, glycerol triacetate, butoxy diethylene glycol acetate, methoxy triethylene glycol acetate, dimethyl ether of propylene glycol, N-methyl-2 pyrrolidone, tri-n-butylphosphate, tetrahydrothiophene 1-1 dioxide, di-isopropanolamine. The drawings depict the preferred monoethanolamine (or ethanolamine) embodiments.

Figure 1:
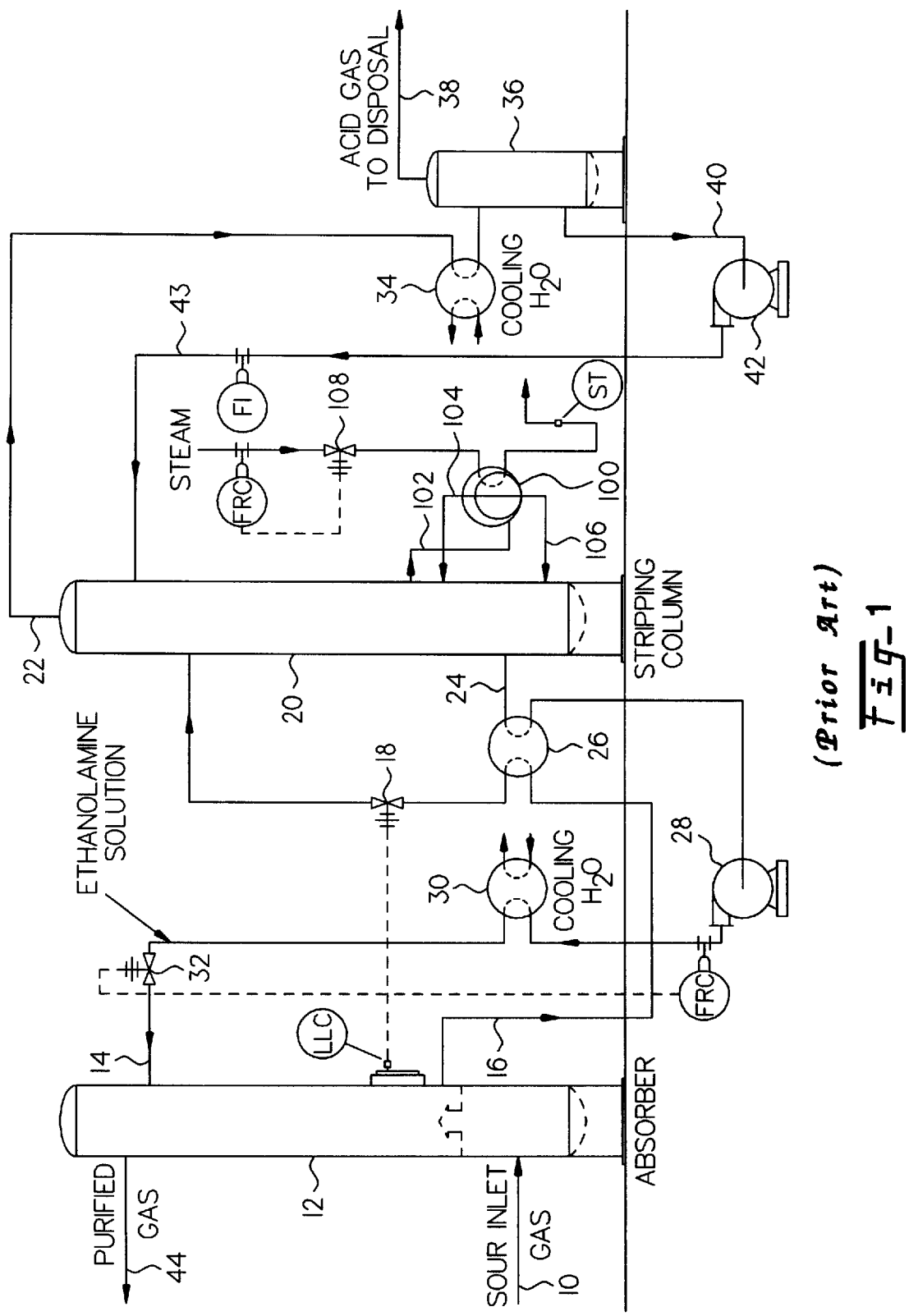
FIG. 1 is a flow chart of a prior art alkanolamine absorbent process.

FIG. 1 shows a flow scheme for a prior art monoethanolamine system. Sour inlet gas 10 (e.g., raw synthesis gas) containing $CO_2$, $H_2S$, cyanide and ammonia is introduced into the bottom of an absorber column 12 and a monoethanolamine stream 14 is introduced at the top of absorber column 12. The monoethanolamine reacts with acid gases in the sour gas to provide a rich aqueous absorbent stream 16. Rich aqueous absorbent stream 16 exits from the bottom of absorber column 12, is heated, passes through valve 18 controlled by a liquid level control (LLC) and is introduced near the top of a stripping column 20. The rising steam in stripping column 20 strips the acid gases from the solution. The acid gases pass through a reflux section at the top of stripping column 20 to form an overhead vapor stream 22 rich in acid gases, which exits the top of stripping column 20. A lean aqueous absorbent solution 24 exits the bottom of stripping column 20, passes through heat exchanger 26, pump 28, heat exchanger 30 and flow ratio controlled (FRC) valve 32 before being introduced near the top of absorber column 12 at an elevated pressure.

The alkanolamine solution coming off the bottom packed or trayed section of stripping column 20 is reboiled in a reboiler 100 adjacent to the column. Liquid 102 enters reboiler 100, where it is heated to provide to the stripping column 20 a reboiled alkanolamine/steam stream 104 and a regenerated alkanolamine stream 106. Steam is provided to the reboiler via flow ratio controlled (FRC). controlled valve 108. Steam trap (ST) is provided along a outlet line from reboiler 100.

Overhead vapor stream 22 is cooled by heat exchanger 34 to condense the monoethanolamine and steam, and is conveyed to a separator 36. The resulting acid gas rich stream 38 passes from the top of separator 36 prior to disposal or use in further processes. An alkanolamine rich aqueous solution 40 passes from the bottom of separator 36 through pump 42 past flow indicator (Fl) and into the reflux section of stripping column 20 via stream 43, to minimize the loss of monoethanolamine with the acid gases. Purified gas stream 44 exits the top of absorber column 12.

Figure 2:
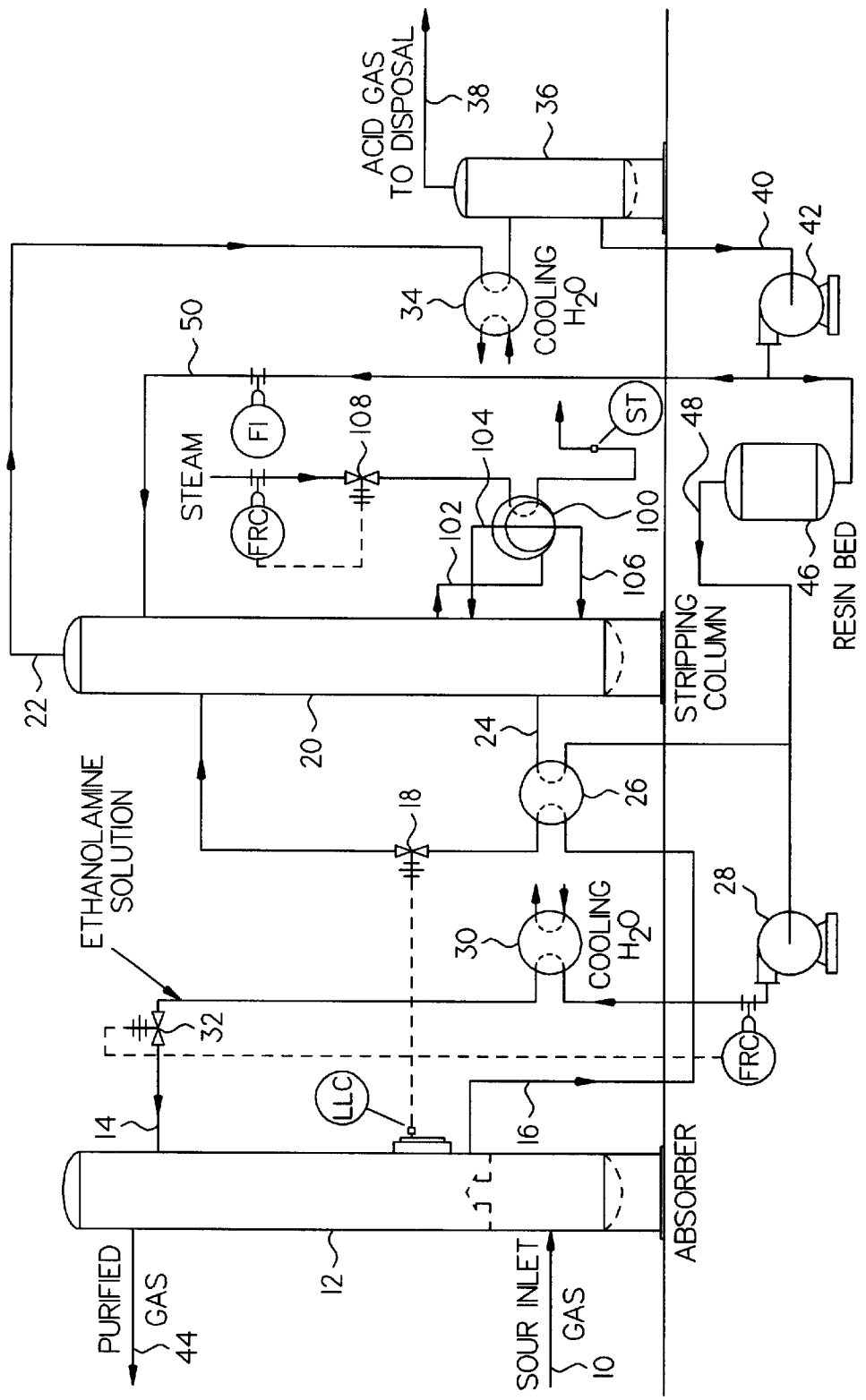
FIGS. 2 and 3 are flow charts of different embodiments of an alkanolamine absorbent process of the invention.
Figure 3:
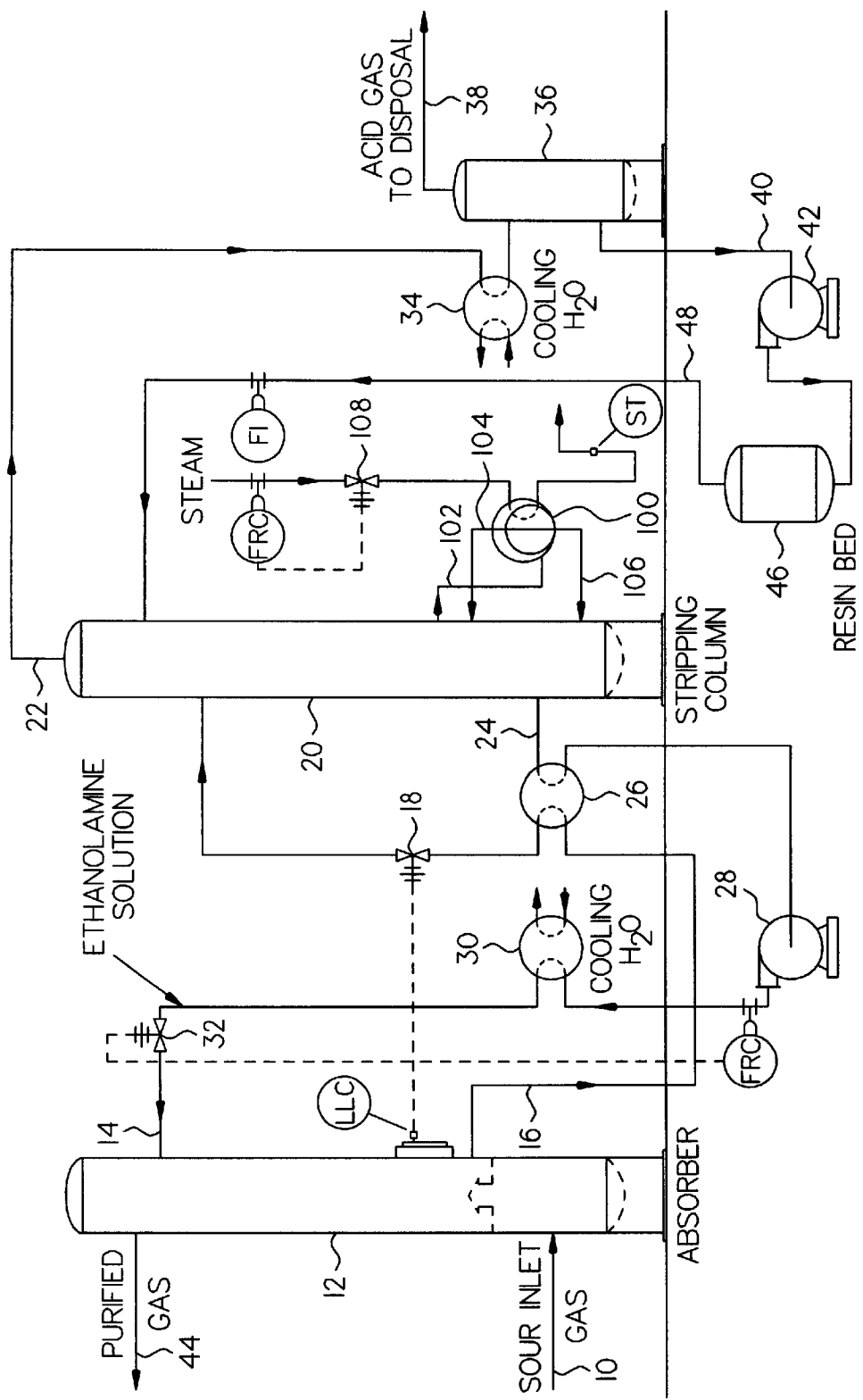

FIGS. 2 and 3 show alternative embodiments of an alkanolamine system of the invention, wherein at least a portion of alkanolamine rich aqueous solution 40 passing from the bottom of separator 36 through pump 42 is introduced into resin bed 46.

Resin bed 46 preferably contains an anionic resin, most preferably a Type II strong base anionic resin, capable of removing corrosive contaminating anions, such as thiocyanate and carbamate. Strong base anion exchange resins are defined as having fixed tertiary amine anion exchange sites which are positively charged at any pH (as opposed to weak base anion exchange resins, which are not positively charged at any pH). Type II resins contain alkanolamine groups- Examples of Type II strong base anion exchange resins suitable for use in the invention include styrene-divinylbenzene resins with quaternary alkanolamine groups attached to the polymer framework, such as Resintech™ SBG-II (Resintech), lonac™ ASB-II (Sybron), Amberlite™ IRA-410 (Rohm and Haas) and various resins available from Dow Chemical under the DOWEX trademark. Additional suitable anion exchange resins include, e.g., weak base anionic exchange resin.

Resin bed 46 operates at near ambient temperature and pressure corresponding to the conditions of the cooled reflux stream. Typical bed sizing would allow for 20 minute contact time and a bed diameter equivalent to allow a ratio of flow rate of two gallons per minute per square foot of surface area.

In the preferred embodiment depicted in FIG. 2, one portion (e.g., at least 10 vol. %, preferably at least 80 vol. %) of alkanolamine rich aqueous solution 40 passing from the bottom of separator 36 through pump 42 is introduced into resin bed 46 and a minor portion (e.g., not more than 90 vol. %, preferably not more than 20 vol. %) of untreated reflux 50 is returned to the top of the stripping column. The effluent 48 of resin bed 46 is introduced into the main circulating alkanolamine stream (i.e., lean aqueous absorbent solution 24) prior to this stream being increased in pressure and returned to absorber column 12.

In the alternative embodiment depicted in FIG. 3, all of alkanolamine rich aqueous solution 40 passing from the bottom of separator 36 through pump 42 is introduced into resin bed 46. Resin bed effluent 48 is returned to an upper portion of stripping column 20.

After a period of time, resin bed 46 is taken off-line and regenerated with caustic prior to being returned to operation. Downtime will be much less frequent than is the case for conventional systems which perform ion exchange on the circulating alkanolamine solution (i.e., lean aqueous absorbent solution 24) passed from the bottom of stripping column 20, as the circulating alkanolamine stream is large in relation to the reflux stream treated in accordance with the invention.

The invention will be illustrated in more detail with reference to the following Example, but it should be understood that the present invention is not deemed to be limited thereto.

EXAMPLE

A monoethanolamine treatment facility was used to treat a synthetic gas containing $CO_2$, cyanide, and ammonia in accordance with FIG. 1 for a period of 3 years. After this period, it was found that corrosion in the reflux section prevented the return of most of the reflux stream to the top of the stripping column. Reintroduction of this stream into the regenerated circulating monoethanolamine stream resulted in very rapid corrosion of the pressure letdown valve on the acid gas laden monoethanolamine between the absorber and the stripping column. Reintroduction of the stream near the top of the stripping column below the reflux section resulted in high levels of iron and chrome in the circulation monoethanolamine solution indicating significant corrosion occurring in the system.

After modifying the facility to perform the process of FIG. 2 for a period of one day using a Type II strong base anionic resin bed (i.e., 28 cubic feet of DOWEX MSA-2 anion exchange resin) the ionically-exchanged reflux stream was successfully introduced into the regenerated circulating monoethanolamine stream without causing either corrosion of the pressure letdown valve or increases in chrome and iron content in the circulating monoethanolamine stream.

While the invention has been described in detail and with reference to specific examples thereof, it will be apparent to one skilled in the art that various changes and modifications can be made therein without departing from the spirit and scope thereof.

What is claimed is:

1. In a process for removing $CO_2$ and/or $H_2S$ from a gas mixture containing as impurities $CO_2$ and/or $H_2S$ and at least one other impurity selected from the group consisting of a cyanide and ammonia, wherein:

said gas mixture is conveyed to an absorber vessel and contacted with an aqueous absorbent solution containing an acid gas removal solvent to remove $CO_2$ and/or $H_2S$ from said gas mixture and form a rich aqueous absorbent solution enriched in $CO_2$ and/or $H_2S$ removed from said gas mixture;

said rich aqueous absorbent solution is conveyed from said absorber vessel to a stripping vessel, and thermally stripped of $CO_2$ and/or $H_2S$ to form a lean aqueous absorbent solution depleted of $CO_2$ and/or $H_2S$, and an overhead vapor stream rich in $CO_2$ and/or $H_2S$ and said at least one other impurity;

said lean aqueous absorbent solution is recycled from said stripping vessel to said absorber vessel to absorb additional amounts of said gas mixture;

said overhead vapor stream is cooled in a heat exchanger to provide a two phase outlet stream and said two phase outlet stream is separated in a separator vessel to provide an acid gas rich stream and an acid gas removal solvent rich aqueous solution; and recycling said acid gas removal solvent rich aqueous solution for further use in said process, the improvement comprising contacting at least a portion of said acid gas removal solvent rich aqueous solution with an anion exchange resin to remove from said acid gas removal solvent rich aqueous solution at least a part of said at least one other impurity prior to said recycling of said acid gas removal solvent rich aqueous solution for further use in said process.

2. The process of claim 1, wherein said gas mixture contains impurities comprising $CO_2$ and/or $H_2S$, and cyanide and/or ammonia.

3. The process of claim 2, wherein said gas mixture further comprises at least one member selected from the group consisting of carboxylic acids and mixtures thereof.

4. The process of claim 1, wherein said acid gas removal solvent is an alkanolamine selected from the group consisting of monoethanolamine, diethanolamine, methyl diethanolamine, diisopropanol amine, triethanol amine methanol, potassium carbonate, diglycolamine, propylene carbonate, glycerol triacetate, butoxy diethylene glycol acetate, methoxy triethylene glycol acetate, dimethyl ether of propylene glycol, N-methyl-2 pyrrolidone, tri-n-butylphosphate, tetrahydrothiophene 1-1 dioxide, di-isopropanolamine.

5. The process of claim 1, wherein said acid gas removal solvent is monoethanolamine.

6. The process of claim 1, wherein said anion exchange resin is a Type II strong base anionic resin.

7. The process of claim 1, wherein said anion exchange resin is a member selected from the group consisting of weak base anionic resins.

8. The process of claim 1, wherein a minor portion of said acid gas removal solvent rich aqueous solution is conveyed to an upper portion of said stripping vessel without being ionically exchanged, and a major portion of said acid gas removal solvent rich aqueous solution is contacted with said anion exchange resin and then conveyed to an upper portion of said absorber vessel.

9. The process of claim 8, wherein said gas mixture contains impurities comprising $CO_2$ and/or $H_2S$, and cyanide and/or ammonia, said acid gas removal solvent is monoethanolamine, and said anion exchange resin is a Type II base anionic resin.

10. The process of claim 1, wherein all of said acid gas removal solvent rich aqueous solution is conveyed from said separator vessel to said anion exchange resin, and an effluent of said anion exchange resin is conveyed to an upper portion of said stripping vessel.

11. The process of claim 1, wherein said anion exchange resin is periodically taken offline and regenerated by caustic.

12. An acid gas removal solvent processing apparatus adapted to perform the process of claim 1, said apparatus comprising:

an absorber vessel comprising a sour gas mixture inlet and a rich aqueous absorbent solution outlet below a purified gas outlet and an acid gas removal solvent rich aqueous solution inlet;

a stripping vessel comprising in order from top to bottom, an overhead vapor outlet, a recycled reflux inlet, a rich aqueous absorbent solution inlet and a lean aqueous absorbent solution outlet, wherein said rich aqueous absorbent solution inlet is in fluid communication with said rich aqueous absorbent solution outlet and said lean aqueous absorbent solution outlet is in fluid communication with said acid gas removal solvent rich aqueous solution inlet;

a heat exchanger comprising an overhead vapor stream inlet and a two phase stream outlet on one side and a coolant stream inlet and a coolant stream outlet on the other side wherein said overhead vapor stream inlet is in fluid communication with said overhead vapor stream outlet;

a separator vessel comprising in order from top to bottom, an acid gas rich stream outlet, a two phase stream inlet, and an alkanolamine rich aqueous solution outlet, wherein said two phase stream inlet is in fluid communication with said two phase stream outlet and said alkanolamine rich aqueous solution outlet is in fluid communication with said recycled reflux inlet; and a resin bed comprising said anion exchange resin, a resin bed inlet, and a resin bed outlet, wherein said resin bed inlet is in fluid communication with said alkanolamine rich aqueous solution outlet, and said resin bed outlet is in fluid communication with said alkanolamine rich aqueous solution inlet.

13. An alkanolamine processing apparatus adapted to perform the process of claim 1, said apparatus comprising:

an absorber vessel comprising a sour gas mixture inlet and a rich aqueous absorbent solution outlet below a purified gas outlet and an alkanolamine rich aqueous solution inlet;

a stripping vessel comprising in order from top to bottom, an overhead vapor outlet, a recycled reflux inlet, a rich aqueous absorbent solution inlet and a lean aqueous absorbent solution outlet, wherein said rich aqueous absorbent solution inlet is in fluid communication with said rich aqueous absorbent solution outlet and said lean aqueous absorbent solution outlet is in fluid communication with said alkanolamine rich aqueous solution inlet;

a separator vessel comprising in order from top to bottom, an acid gas rich stream outlet, a rich reflux gas inlet, and an alkanolamine rich aqueous solution outlet, wherein said rich reflux gas inlet is in fluid communication with said rich reflux gas outlet and said alkanolamine rich aqueous solution outlet is in fluid communication with said recycled reflux inlet; and a resin bed comprising said anion exchange resin, a resin bed inlet, and a resin bed outlet, wherein said resin bed inlet is in fluid communication with said alkanolamine rich aqueous solution outlet, and said resin bed outlet is in fluid communication with said alkanolamine rich aqueous solution inlet.

a heat exchanger comprising an overhead vapor stream inlet and a two phase stream outlet on one side and a coolant stream inlet and a coolant stream outlet on the other side wherein said overhead vapor stream inlet is in fluid communication with said overhead vapor stream outlet;

a separator vessel comprising in order from top to bottom, an acid gas rich stream outlet, a two phase stream inlet, and an alkanolamine rich aqueous solution outlet, wherein said two phase stream inlet is in fluid communication with said two phase stream outlet; and a resin bed comprising said anion exchange resin, a resin bed inlet, and a resin bed outlet, wherein said resin bed inlet is in fluid communication with said alkanolamine rich aqueous solution outlet, and said resin bed outlet is in fluid communication with said recycled reflux inlet.

* * * * *